(12) United States Patent
Nicolazzi et al.

(10) Patent No.: US 8,366,631 B2
(45) Date of Patent: Feb. 5, 2013

(54) SYSTEM AND METHOD FOR DETECTING RESPIRATORY EVENTS

(75) Inventors: Pascal Nicolazzi, Gondreville (FR); Véronique Grillier-Lanoir, Besancon (FR); Bruno Flemmich, Villers-les-Nancy (FR); Yves Gaudard, Malzeville (FR); Hossein Nadjafizadeh, Villers lès Nancy (FR)

(73) Assignee: Covidien LP, Mansfield, MA (US)

( * ) Notice: Subject to any disclaimer, the term of this patent is extended or adjusted under 35 U.S.C. 154(b) by 1527 days.

(21) Appl. No.: 11/863,470

(22) Filed: Sep. 28, 2007

(65) Prior Publication Data

US 2008/0097234 A1     Apr. 24, 2008

(30) Foreign Application Priority Data

Sep. 29, 2006   (FR) ...................................... 06 08598

(51) Int. Cl.
*A61B 5/08* (2006.01)
(52) U.S. Cl. ........................................ 600/538; 600/529
(58) Field of Classification Search ............ 600/529–543
See application file for complete search history.

(56) References Cited

U.S. PATENT DOCUMENTS

| | | | | |
|---|---|---|---|---|
| 5,117,819 | A | 6/1992 | Servidio et al. | 128/204.18 |
| 6,349,724 | B1 | 2/2002 | Burton et al. | 128/204.18 |
| 6,626,175 | B2 * | 9/2003 | Jafari et al. | 128/204.21 |
| 6,814,074 | B1 * | 11/2004 | Nadjafizadeh et al. | 128/204.23 |
| 2005/0076908 | A1 | 4/2005 | Lee et al. | 128/204.23 |
| 2005/0217674 | A1 | 10/2005 | Burton et al. | 128/204.23 |
| 2006/0000475 | A1 | 1/2006 | Matthews et al. | 128/204.21 |
| 2006/0102179 | A1 | 5/2006 | Rapoport et al. | 128/204.23 |
| 2007/0118054 | A1 | 5/2007 | Pinhas et al. | 600/587 |
| 2008/0053440 | A1 | 3/2008 | Farrugia | 128/204.23 |

FOREIGN PATENT DOCUMENTS

| | | |
|---|---|---|
| EP | 1 270 036 A2 | 1/2003 |
| WO | 92/11054 A1 | 7/1992 |
| WO | 99/61088 A1 | 12/1999 |
| WO | WO 9961088 A1 * | 12/1999 |
| WO | 03/075991 | 9/2003 |
| WO | WO 03075991 A1 * | 9/2003 |

OTHER PUBLICATIONS

International Search Report, PCT/US2007/079882, 4 pages, mailed on Jul. 17, 2008.
International PCT Search and Written Opinion, PCT/US2007/079874, 14 pages, Mailed Jul. 17, 2008.

* cited by examiner

*Primary Examiner* — Navin Natnithithadha
*Assistant Examiner* — Karen Toth

(57) ABSTRACT

A method for determining the respiratory flow of a patient receiving bi-level respiratory therapy is provided. The method may include measuring the total air flow through a breathing area at a time approximately when the patient has completed exhalation, measuring the pressure in the breathing area, determining a constant representing a corrective flow factor by dividing the measured total air flow by the square root of the measured pressure, and determining the patient's respiratory flow by subtracting from a subsequent total air flow the product of constant and the square root of a subsequent pressure.

3 Claims, 4 Drawing Sheets

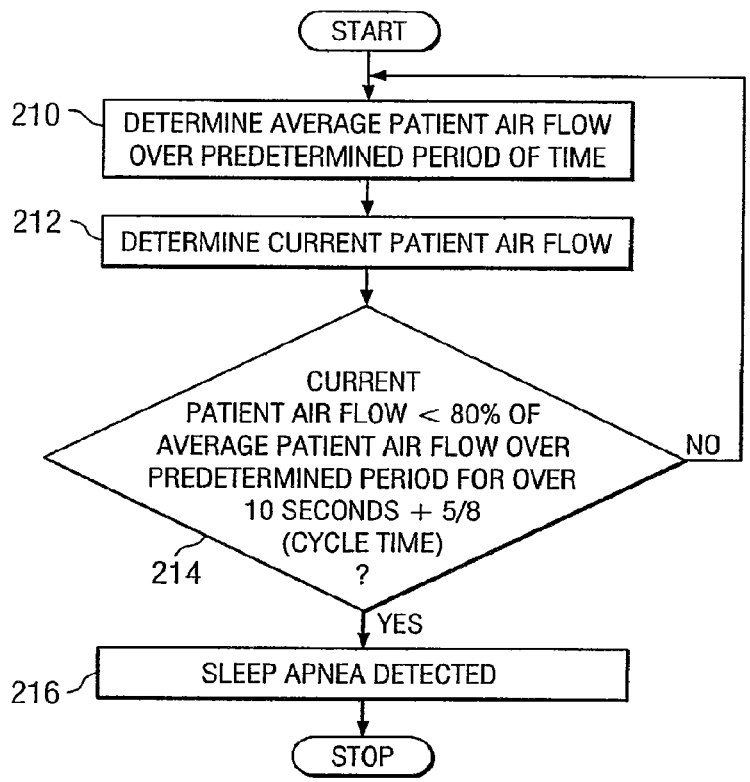
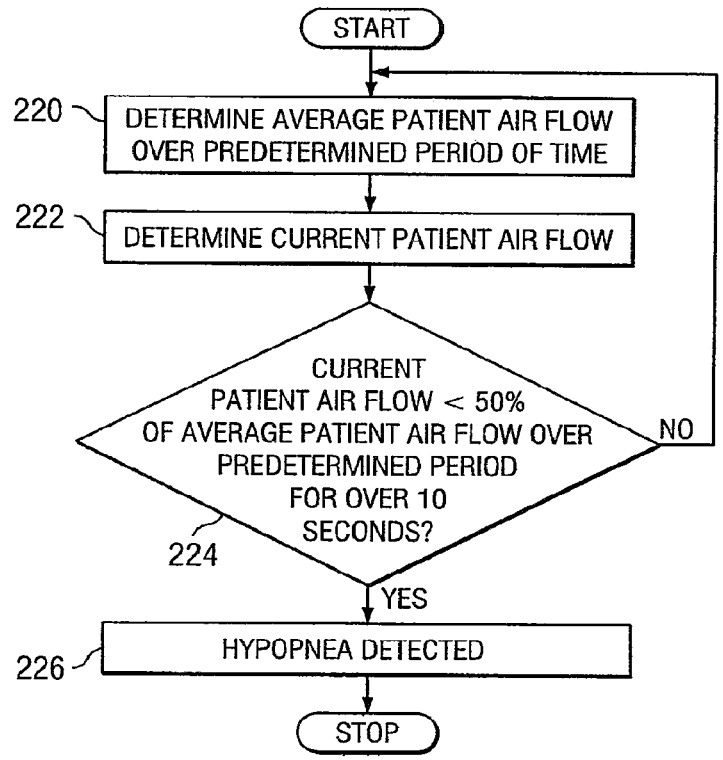

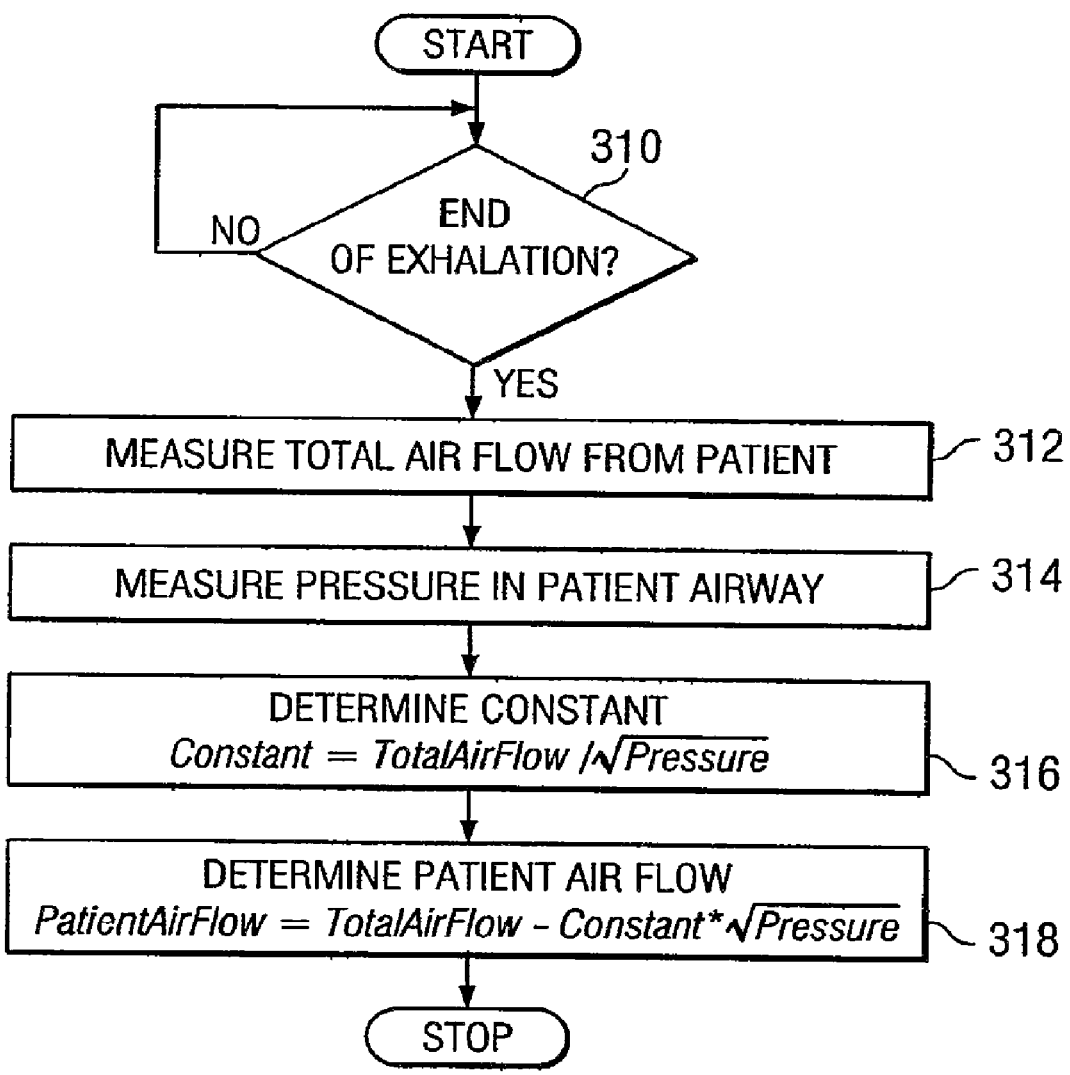

SYSTEM AND METHOD FOR DETECTING RESPIRATORY EVENTS

RELATED APPLICATION

This application claims priority from French Patent Application No. 06/08598, which was filed on Sep. 29, 2006, and is incorporated herein by reference in its entirety.

TECHNICAL FIELD

The present disclosure relates generally to the field of respiratory therapy, e.g., a system and method for detecting respiratory events.

BACKGROUND

Sleep apnea occurs when a person stops breathing during sleep. An apnea may be defined as the cessation or reduction of airflow for a certain period of time. Apneas may lead to decreased blood oxygenation and thus to the disruption of sleep. With some apneas, the airway is open, and the patient is merely not attempting to breathe. With other apneas, the airway is closed. The airway may also be partially obstructed (i.e., narrowed). This may also lead to decreased ventilation, decreased blood oxygenation, and/or disturbed sleep.

A common form of treatment for apneas is the administration of Continuous Positive Airway Pressure (CPAP). CPAP treatment acts as a pneumatic splint of the airway by the provision of a constant positive pressure to the patient usually in the range 3 to 20 centimeters of water (cm $H_2O$). Another form of treatment for apneas is the administration of bi-level (or "BiPAP") treatment. With bi-level treatment, one pressure level is provided while a patient is inhaling and a second, generally lower, pressure level is provided while the patient is exhaling. CPAP and bi-level treatments may be applied over a predetermined period of time, where the pressure applied to a patient is "ramped up" over time. For instance, a patient may begin the sleep process with a pressure being applied at one value and the pressure may be gradually raised to a second pressure over a predetermined ramp time (e.g., less than forty-five minutes). The purpose of such ramp up process is to allow the patient to fall asleep while a relatively low pressure is being applied, and raise the pressure to the treatment pressure after the patient is asleep in order to treat apnea-type events. The higher, treatment level pressure is generally not applied while the patient is awake because it may be uncomfortable for the patient and may hinder the patient's ability to fall asleep. However, the time it takes for a patient to fall asleep (referred to as "latency") may be highly variable from night to night and/or from patient to patient. In some instances, the patient may fall asleep and experience apnea before the pressure has ramped up to the treatment pressure level, in which case the pressure may be insufficient to prevent or treat the apnea. In other instances, the patient may still be awake when the pressure has ramped up to the treatment pressure level (or other relatively high pressure), which may be uncomfortable and which may hinder the patient's ability to fall asleep, as discussed above.

With both CPAP and bi-level therapy, pressurized air is supplied to the airway of the patient by a motor driven blower (or other suitable gas delivery system) that delivers the pressurized air through a connection system (e.g., a breathing circuit or air delivery hose) to one or more breathing passages of the patient (e.g., the patient's nose and/or mouth) via a mask sealingly engaged against the patient's face. An exhaust port may be provided proximate to the mask to allow exhaled gasses to escape. The mask can take various forms, e.g., a nose, mouth, or face mask, nasal prongs, pillows or cannulae.

SUMMARY

According to one embodiment of the present disclosure, a method for determining the respiratory flow of a patient receiving bi-level respiratory therapy is provided. The method may include measuring the total air flow through a breathing area at a time approximately when the patient has completed exhalation, measuring the pressure in the breathing area, determining a constant representing a corrective flow factor by dividing the measured total air flow by the square root of the measured pressure, and determining the patient's respiratory flow by subtracting from a subsequent total air flow the product of constant and the square root of a subsequent pressure.

According to another embodiment of the present disclosure, a system for determining the respiratory flow of a patient receiving bi-level respiratory therapy is disclosed. The system may include a breathing device defining a breathing area, a flow sensor operable to measure the total air flow through the breathing area at a time approximately when the patient has completed exhalation, a pressure sensor operable to measure the pressure in the breathing area, and a processor. The processor may be operable to determine a constant representing a corrective flow factor by dividing the measured total air flow by the square root of the pressure, and to determine the patient's respiratory flow by subtracting from a subsequent total air flow the product of the constant and the square root of a subsequent pressure.

According to another embodiment of the present disclosure, a computer-readable storage medium storing a set of instructions executable on a processor is disclosed. The set of instructions includes instructions for determining airflow from a patient receiving bi-level respiratory therapy by determining a constant representing a corrective flow factor by dividing a total air flow at a breathing area, measured at a time approximately when the patient has completed exhalation, by the square root of a pressure measured at the breathing area, and subtracting from a subsequent total air flow the product of the constant and the square root of a subsequent pressure.

According to another embodiment of the present disclosure, a method for detecting a respiratory event in a patient while using a breathing device defining a breathing area operating in bi-level mode is disclosed. The method includes measuring the total air flow through the breathing area at a time approximately when the patient has completed exhalation; measuring the pressure in the breathing area; determining a constant representing a corrective flow factor by dividing the measured total air flow by the square root of the pressure; determining the patient's respiratory flow by subtracting from a subsequent total air flow the product of the constant and the square root of a subsequent pressure; determining an average flow for a plurality of breathing cycles; and determining the occurrence of a respiratory event by determining if the patient's respiratory flow is less than a predetermined percentage of the determined average flow.

According to another embodiment of the present disclosure, a system for detecting a respiratory event in a patient while undergoing a bi-level respiratory therapy is disclosed. The system includes a breathing device defining a breathing area, a flow sensor operable to measure the total air flow through the breathing area at a time approximately when the patient has completed exhalation, a pressure sensor operable to measure the pressure in the breathing area, and a processor. The processor may be operable to determine a constant representing a corrective flow factor by dividing the measured total air flow by the square root of the pressure; determine the patient's respiratory flow by subtracting from a subsequent total air flow the product of the constant and the square root of a subsequent pressure; determine an average flow for a plurality of breathing cycles; and determine the occurrence of a respiratory event by determining if the patient's respiratory flow is less than a predetermined percentage of the determined average flow.

According to another embodiment of the present disclosure, a computer-readable storage medium storing a set of instructions executable on a processor, the set of instructions is disclosed. The medium may include instructions for determining respiratory flow from a patient receiving bi-level respiratory therapy by determining a constant representing a corrective flow factor by dividing a total air flow at a breathing area, measured at a time approximately when the patient has completed exhalation, by the square root of a pressure measured at the breathing area, and subtracting from a subsequent total air flow the product of the constant and the square root of a subsequent pressure. The medium may further include instructions for determining an average flow for a plurality of breathing cycles, and instructions for determining the occurrence of a respiratory event by determining if the patient's respiratory flow is less than a predetermined percentage of the determined average flow.

According to another embodiment of the present disclosure, a system for detecting a respiratory event in a patient while undergoing a bi-level respiratory therapy is disclosed. The system includes breathing means defining a breathing area, flow sensing means for measuring the total air flow through the breathing area at a time approximately when the patient has completed exhalation, pressure sensing means for measuring the pressure in the breathing area, and processing means. The processing means may be configured for: determining a constant representing a corrective flow factor by dividing the measured total air flow by the square root of the pressure; determining the patient's respiratory flow by subtracting from a subsequent total air flow the product of the constant and the square root of a subsequent pressure; determining an average flow for a plurality of breathing cycles; and determining the occurrence of a respiratory event by determining if the patient's respiratory flow is less than a predetermined percentage of the determined average flow.

According to another embodiment of the present disclosure, a system for determining a patient's respiratory flow while undergoing a bi-level respiratory therapy is disclosed. The system includes breathing means defining a breathing area, flow sensing means for measuring the total air flow through the breathing area at a time approximately when the patient has completed exhalation, pressure sensing means for measuring the pressure in the breathing area, and processing means for determining a constant representing a corrective flow factor by dividing the measured total air flow by the square root of the pressure, and for determining the patient's respiratory flow by subtracting from a subsequent total air flow the product of the constant and the square root of a subsequent pressure.

BRIEF DESCRIPTION OF THE DRAWINGS

Some embodiments of the disclosure may be understood by referring, in part, to the following description and the accompanying drawings, in which like reference numbers refer to the same or like parts, and wherein:

FIG. 2A is a flow diagram demonstrating an example method for detecting sleep apnea in a patient, in accordance to one embodiment of the present disclosure;

FIG. 2B is a flow diagram demonstrating an example method for detecting a hypopnea in a patient, in accordance to one embodiment of the present disclosure; and FIG. 3 illustrates an example method of determining a patient's airflow during bi-level breathing assistance, according to one embodiment of the present disclosure.

DETAILED DESCRIPTION

Selected embodiments of the disclosure may be understood by reference, in part, to FIGS. 1A-3, wherein like numbers refer to same and like parts.

In general, the present disclosure describes methods and apparatuses for determining a patient's airflow while the patient is undergoing bi-level respiratory therapy and/or using the determined airflow to detect respiratory events experienced by a patient while the patient is undergoing bi-level respiratory therapy. In addition, the present disclosure describes systems and methods for controlling respiratory therapy (e.g., triggering a ramp function to increase the pressure of gas delivered to a patient) based on detected respiratory events.

Figure 1A:
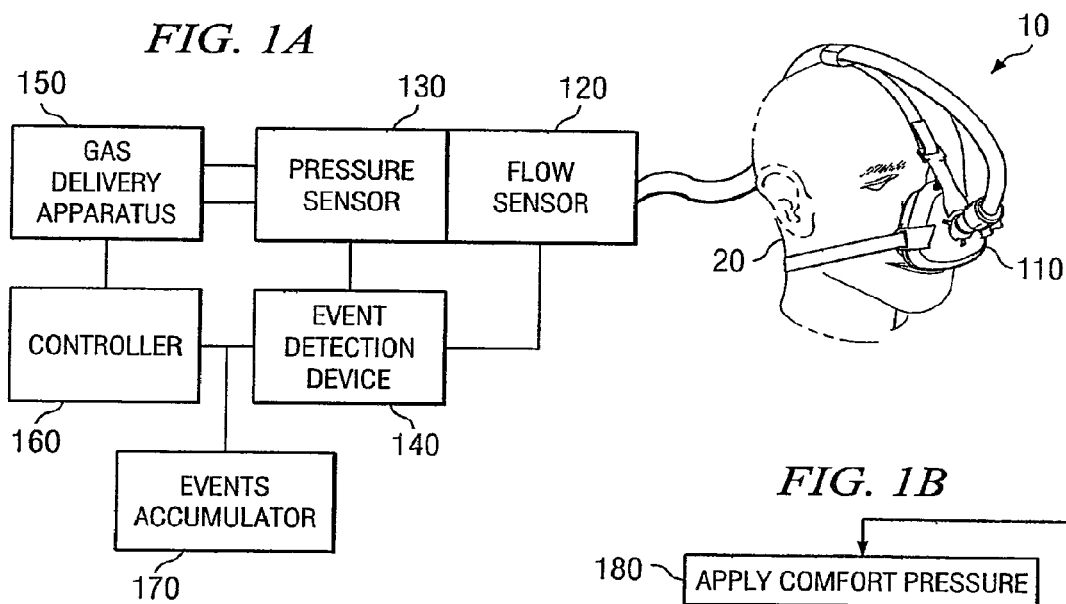
FIG. 1A illustrates an example breathing assistance system for providing breathing assistance to a patient, according to one embodiment of the present disclosure.

FIG. 1A illustrates an example breathing assistance system 10 for providing breathing assistance to a patient 20, according to one embodiment of the present disclosure. Breathing assistance system 10 may include a patient interface 110, one or more flow sensors 120, one or more pressure sensors 130, an event detection device 140, a gas delivery apparatus 150, a controller 160, and/or an events accumulator 170. Breathing assistance system 10 may be configured to deliver gas to patient 20, detect respiratory events associated with patient 20, and/or control respiratory therapy (e.g., trigger a ramp function to increase the pressure of gas delivered to patient 20) in response to the detection of such respiratory events.

In some embodiments, breathing assistance system 10 may operate in either or both of the following modes:

(1) Continuous positive airway pressure mode (CPAP)—gas is delivered to the patient at a constant pressure level over the breath cycle. This pressure level may be determined, e.g., by a physician and may be used to provide respiratory therapy to the patient.

(2) "bi-level" or "BiPAP" mode—gas is delivered to the patient at a first (higher) pressure level during the inhalation portion of the breath cycle and a second (lower) pressure level during the exhalation portion of the breath cycle. The first pressure level may be referred to as the treatment pressure level.

The pressurized gas may be provided and/or delivered by gas delivery apparatus 150. Gas delivery apparatus 150 may include any device or devices configured to generate, supply, and/or deliver gas (e.g., pressurized air) toward patient 20, e.g., a blower, piston-based device, an air pump, a wall outlet through which pressurized air may be supplied, one or more tanks of compressed gas, a compressor, or any other suitable source of pressurized or non-pressurized gas.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. The term "patient" may refer to any person or animal that may receive breathing assistance from system 10, regardless of the medical status, official patient status, physical location, or any other characteristic of the person. Thus, for example, a patient 20 may include any person under official medical care (e.g., hospital patients), a person not under official medical care, a person receiving care at a medical care facility, a person using a home care device (e.g., a home or travel CPAP or BiPAP device), etc.

Patient interface 110 may include any device or devices configured to interface with one or more breathing passages of patient 20 to deliver gas from gas delivery apparatus 150 to patient 20. For example, patient interface 110 may include a mask or nasal pillows positioned over the patient's nose and/or mouth, a patient connection tube directly connected to one or more breathing passages, or any other suitable interface.

A pressure sensor 130 may detect gas pressure at a particular location within system 10 (e.g., the pressure of gas output by gas delivery apparatus 150, the pressure of gas within patient interface 110, and/or the pressure of gas within any gas delivery conduit connected between gas delivery apparatus 150 and patient interface 110. System 10 may include any number of pressure sensors 130 located at any one or more locations of system 10.

A flow sensor 120 may detect gas flow at a particular location within system 10, e.g., gas flow output by gas delivery apparatus 150, gas flow within patient interface 110, and/or gas flow within any gas delivery conduit connected between gas delivery apparatus 150 and patient interface 110. System 10 may include any number of flow sensors 120 located at any one or more locations of system 10. For example, a flow sensor 120 may be located in or proximate patient interface 110 for detecting the gas flow from patient interface 110.

Event detection device 140 may be operable to detect respiratory events experienced by patient 20 based at least on pressure data, flow data, and/or torque data received from sensor 120, sensor 130, and/or gas delivery apparatus 150. Pressure data, flow data, and/or torque data from sensor 120, sensor 130, and/or gas delivery apparatus 150 may be communicated to event detection device 140 in any suitable manner, e.g., by any one or more wireline or wireless links.

Respiratory events may include any breathing phenomena including, for example, an apnea, a hypopnea, snoring, any flow limitation, and/or any combination thereof. Event detection device 140 may communicate one or more detected respiratory events to control controller 160, which may then control gas delivery apparatus 150 to control respiratory therapy delivered to patient 20 based at least on such one or more detected respiratory events. For example, as discussed in greater detail below, controller 160 may control gas delivery apparatus 150 to increase (e.g., ramp up) the pressure of gas delivered to patient 20 from a first pressure level to a second pressure level in response to signals received from event detection device 140 indicating one or more detected respiratory events (e.g., one or more apneas).

Controller 160 may be generally operable to control gas delivery apparatus 150. For example, controller 160 may control the pressure, flow rate, temperature, etc. of gas delivered by gas delivery apparatus 150. Controller 160 may include any variety of analog or digital switches, actuators, or control devices suitable to control gas delivery apparatus 150. Controller 160 may receive data from event detection device 140 and/or events accumulator 170 indicating one or more detected respiratory events, and may control gas delivery apparatus 150 based at least on such data.

In some embodiments, controller 160 may be operable to automatically trigger a ramp function in response to data received from event detection device 140 and/or events accumulator 170 indicating one or more detected respiratory events. For example, controller 160 may automatically trigger a ramp function in response to data received from event detection device 140 indicating a single detected respiratory event. As another example, controller 160 may automatically trigger a ramp function in response to data received from events accumulator 170 indicating a number of detected respiratory events exceeding a predetermined threshold, as discussed below in greater detail.

Triggering a ramp function may include controlling gas delivery apparatus 150 to increase (or "ramp") the pressure of breathing gas delivered toward patient 20 from a first pressure to a second pressure at a predetermined rate. For example, a ramp function may be used to increase the pressure of breathing gas delivered toward patient 20 from a "comfort pressure" to an "effective pressure" at a predetermined rate. The "comfort pressure" may be a relatively low pressure suitable to allow patient 20 to fall asleep. For example, the comfort pressure may be between five and fifteen cm $H_2O$. The "effective pressure" may be a higher pressure sufficient to prevent, reduce the likelihood of, or otherwise resist one or more respiratory events (e.g., apneas, hypopneas, and/or snoring). For example, the effective pressure may be between ten and thirty cm $H_2O$.

In some embodiments, one or both of the comfort pressure and the effective pressure may be set or adjusted by a user. For example, in some embodiments, the effective pressure may be prescribed by a physician, and may represent the appropriate therapy for a particular patient to help alleviate undesirable respiratory events. In other embodiments, one or both of the comfort pressure and the effective pressure may be programmed into the system and may not be adjusted by a user.

A ramp function may be defined as any increase in applied pressure over a non-instantaneous period of time. For example, a ramp function may gradually and smoothly increase the pressure of breathing gas delivered toward patient 20 from a first pressure (e.g., a comfort pressure) to a second pressure (e.g., an effective pressure). Such gradual increase may be either linear or non-linear (e.g., exponential or logarithmic). As another example, a ramp function may increase the pressure of breathing gas delivered toward patient 20 from a first pressure (e.g., a comfort pressure) to a second pressure (e.g., an effective pressure) in a stepped manner.

A ramp function may have a predetermined rate of pressure increase and/or a predetermined time duration. For example, in some embodiments, the ramp function may increase the gas pressure at a rate of between about one cm $H_2O$ per minute and about five cm $H_2O$ per minute. In a particular embodiment, the ramp function may increase the gas pressure at a rate of approximately 1 cm $H_2O$ per minute. However, any other (linear or non-linear) rate of increase may be used to reach the effective pressure. In some embodiments, the type of ramp function (e.g., smooth or stepped, the rate of pressure increase, and/or the time duration of the ramp function) may be set or adjusted by a user. In other embodiments, such parameters may be predetermined and may not be set or adjusted by a user.

As discussed above, detected respiratory events may indicate that patient 20 is asleep, for instance. Increasing the pressure level after one or more detected respiratory events are detected may be desirable because the effective pressure level may be uncomfortable to patient 20 when patient 20 is awake and may disrupt the patient's ability to fall asleep if applied before the patient has fallen asleep. Respiratory events may be detected using any of the methods described below in conjunction with FIGS. 2A through 3 and/or using any other known or suitable method. In addition, suitable methods for detecting respiratory events may be found in U.S. Pat. No. 6,814,074 (the "'074 patent"). By way of example, FIG. 4 of the '074 patent describes a method for detecting flow limitation events which may be used in accordance with the present invention. FIG. 6 of the '074 patent describes a method for detecting hypoventilation and hyperventilation events which may be used in accordance with the present invention. FIG. 12 of the '074 patent describes a method for detecting an acoustic vibration or snoring event which may be used in accordance with the present invention.

Figure 1B:
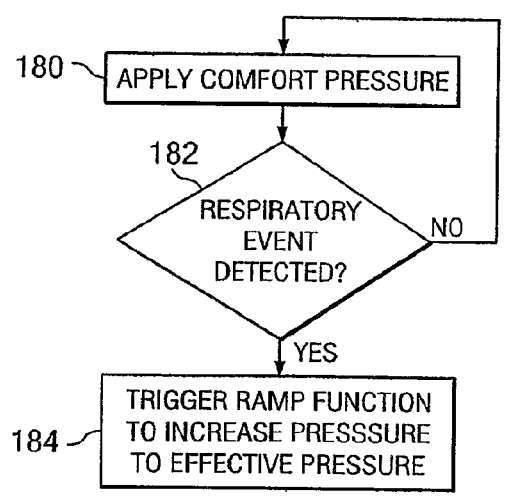
FIG. 1B illustrates an example method for controlling respiratory therapy (e.g., triggering a ramp function) in response to detecting one or more respiratory events, according to one embodiment of the present disclosure.

FIG. 1B illustrates an example method for controlling respiratory therapy (e.g., triggering a ramp function) in response to detecting one or more respiratory events, according to one embodiment of the present disclosure. At step 180, gas may be delivered to a patient 20 at a first pressure, e.g., the comfort pressure. In some embodiments, gas delivery apparatus 150 may deliver gas at the comfort pressure when gas delivery apparatus 150 is turned on. In other embodiments, gas delivery apparatus 150 may deliver gas at another pressure (e.g., the effective pressure) when gas delivery apparatus 150 is turned on, and may then begin delivering gas at the comfort pressure after some preset time (e.g., after a self-test period) or in response to one or more selections made by a user (e.g., in response to the patient pressing an "activate ramp" or "comfort pressure" button). In other embodiments, gas delivery apparatus 150 may begin delivering gas at the comfort pressure after some preset time (e.g., 30 minutes) allowing the patient to fall asleep without pressurized gas being applied. In some embodiments, one or more preset or predetermined times discussed herein may be set or adjusted by a user. In other embodiments, one or more preset or predetermined times discussed herein may be programmed into the system and may not be adjusted by a user.

As indicated at step 182, if a particular respiratory event or combination of respiratory events is detected (e.g., using any of the methods described below in conjunction with FIGS. 2A through 3 and/or using any other known or suitable method), a ramp function may be triggered to increase the pressure of gas delivered to patient 20 from the comfort pressure to an effective pressure, as indicated at step 184.

In bi-level mode, where different pressure levels are applied to the patient during the inhalation and exhalation portions of the breath cycle, one or both of the pressure levels may be increased at step 184. For example, both the inhalation pressure level and the exhalation pressure level may be increased at step 184, either at different rates or at the same rate. As another example, the inhalation pressure level but not the exhalation pressure level may be increased at step 184. As another example, the exhalation pressure level but not the inhalation pressure level may be increased at step 184.

The ramp function may be triggered by the detection of a single respiratory event. Alternatively, the ramp function may be triggered by the detection of a combination or accumulation of respiratory events. In some embodiments, respiratory events may be assigned scaled or weighted values, which may depend, e.g., on the type and/or severity of the event. Events accumulator 170 may weight detected respiratory events and sum (or accumulate) the weighted values for detected respiratory events over time. Events accumulator 170 may compare a running sum of weighted values for detected respiratory events over a moving period of time to a threshold. If the sum exceeds the threshold, events accumulator 170 may notify controller 160 such that controller 160 may trigger the ramp function.

For example, each detected apnea may be assigned a value of 25, each detected hypopnea a value of 10, each detected flow limitation a value of 5, each detected snoring incident a value of 1, etc. The values for these detected events can be accumulated over a moving period of time, e.g., five minutes. If the accumulated value of the weighted events exceeds a predetermined value, e.g., 25, during any five minute time period, the ramp function may be triggered.

Figure 1C:
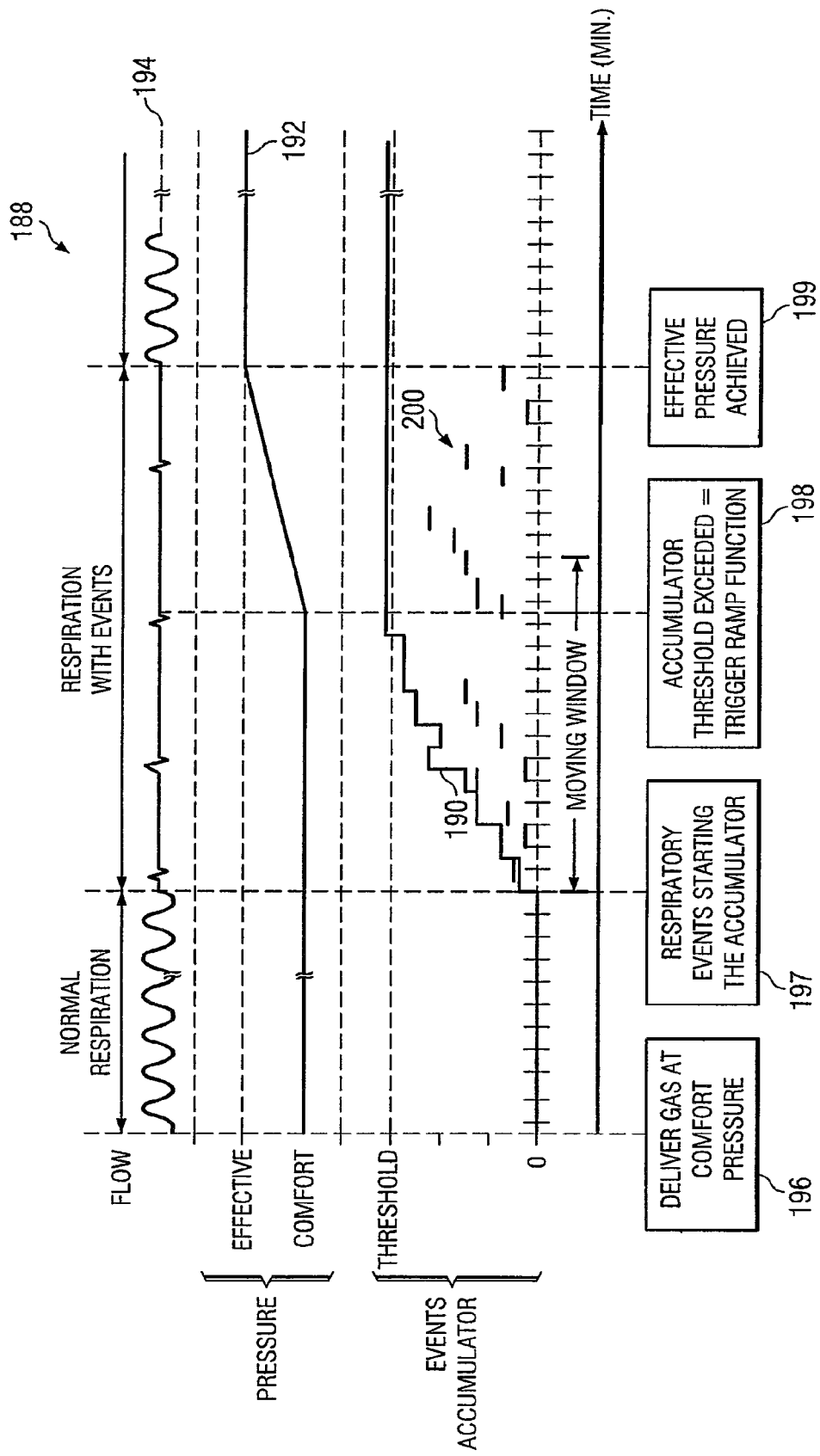
FIG. 1C is a graph illustrating the management of respiratory therapy provided to a patient in an example situation, according to one embodiment of the present disclosure.

FIG. 1C is a graph 188 illustrating the management of respiratory therapy provided to a patient 20 using system 10 in an example situation, according to on embodiment of the disclosure. In particular, FIG. 1C illustrates delivery of gas to a patient 20 at a comfort pressure, detection of multiple respiratory events, the triggering of a ramp function in response to an accumulated value of respiratory events exceeding a predetermined threshold value, and the increase in pressure from the comfort pressure to the effective pressure according to the triggered ramp function.

The horizontal axis of graph 188 represents time. The vertical axis of graph 188 is used to indicate three different parameters:

(1) an accumulated value of respiratory events, indicated at 190, (2) the pressure of gas delivered to patient 20 (e.g., as measured by one or more pressure sensors 130), indicated at 192, and (3) a measure of the patient's breathing flow (e.g., as measured by one or more flow sensors 120), indicated at 194.

At time 196, gas may begin to be delivered to patient 20 at a comfort pressure (e.g., five to fifteen cm $H_2O$). For example, this may represent the point at which gas delivery apparatus 150 is turned on or the point at which the comfort pressure is selected by a user. Sometime after time 196 and before time 197, patient 20 may fall asleep. At time 197, the patient's airflow, indicated by line 194, may become significantly reduced or otherwise affected, which may indicate the occurrence of one or more respiratory events (e.g., apnea or hypopneas), indicated by dashes 200.

As respiratory events are detected by event detection device 140, event accumulator 170 may weight each respiratory event and maintain a weighted sum of detected events, as indicated by accumulated value 190. In this example, event accumulator 170 maintains a running weighted sum for events occurring within a moving five minute window. If accumulated value 190 exceeds (e.g., equals or surpasses) a predetermined threshold value within the moving five minute window, the ramp function is triggered. In this example, accumulator value 190 exceeds the predetermined threshold value within the moving five minute window at time 198. Once the ramp function is triggered, the pressure 192 of gas delivered to patient 20 is ramped up at a predetermined rate until the effective pressure is reached at time 199.

In CPAP mode, the ramp function may increase the pressure level regardless of the patient's breathing cycles. In bi-level mode, the ramp function may increase one or both of the exhalation pressure and inhalation pressure, at either the same rate or at different rates, until the effective pressure is reached. Although FIG. 1C illustrates an example in which the ramp function is triggered upon detection of multiple respiratory events, in other embodiments or situations the ramp function may be triggered upon detection of a single respiratory event. For example, a single apnea may be assigned a weighted value that exceeds the threshold value such that detection of a single apnea triggers the ramp function. As another example, respiratory events are not weighted and any detected respiratory event may trigger the ramp function. Additional details of certain embodiments of the disclosure are described below with reference to FIGS. 2A through 3.

The definition of an apnea may depend on whether the breathing apparatus is applying bi-level or CPAP therapy. In CPAP mode or during the application of CPAP therapy, an apnea may be defined as the cessation of airflow in a patient for a predetermined period of time, e.g., ten seconds plus five-eighths of the patient's breath cycle time. The cessation of airflow may be detected based on data received from any sensor(s) and/or other device(s). For example, in some embodiments, the cessation of airflow may be detected using a torque signal generated by gas delivery apparatus 150 (e.g., a blower or other device). For example, the torque signal may be the electrical drive signal of apparatus 150. During CPAP therapy, the torque signal may indicate whether the patient is inhaling, exhaling, or not breathing because the patient's breathing creates changes in the torque signal value. For instance, a patient's inhalation may decrease the torque signal value, whereas a patient's exhalation may increase the torque signal value. However, when a patient stops breathing, no change in the torque signal is expected. When no change in the torque signal is detected for a predetermined period of time (e.g., 10 seconds plus five-eights of a breathing cycle time), an apnea may be detected in CPAP mode.

In bi-level mode or during the application of bi-level therapy, an apnea may be defined as a reduction in patient airflow below a predetermined threshold for a predetermined period of time, e.g., ten seconds plus five-eighths of the patient's breath cycle time. In some embodiments, the predetermined threshold may be a particular percentage (e.g., 80%) of an average airflow determined for the patient. The reduction in airflow may be detected based on data received from any sensor(s) and/or other device(s). For example, in some embodiments, the reduction of airflow may be detected using one or more flow sensors 120 (e.g., as discussed below regarding FIG. 2A).

FIG. 2A is a flow diagram demonstrating an example method for detecting sleep apnea in a patient during bi-level therapy, in accordance to one embodiment of the present disclosure. The method discussed below for detecting apneas during bi-level therapy may be implemented, for example, using event detection device 140 of system 10 shown in FIG. 1. At step 210, a patient's average airflow over a predetermined period of time or a particular number of breathing cycles may be determined, e.g., using one or more flow sensors 120. Any suitable number of breathing cycles (e.g., eight cycles) may be used. At step 212, the current patient airflow may be determined, e.g., using one or more flow sensors 120. Example methods for determining the air flow of a patient are described below with reference to FIG. 3. At step 214, the current patient airflow determined at step 212 is compared to a threshold percentage (e.g., 80%) of the average patient airflow determined at step 210. If the current patient airflow is less than the threshold percentage of the average patient airflow over a particular period of time, a sleep apnea event is detected at step 216. The particular period of time can vary and can be selected as appropriate for determining the presence of an apnea in a particular patient. For example, the particular period of time may be ten seconds plus five-eighths of the patient's breath cycle time. However, any suitable period of time determined appropriate for indicating an apnea may be used. Thus, in one example, a sleep apnea event may be detected if the patient's current air flow falls below 80% of the patient's average air flow for a period of ten seconds plus five-eighths of the patient's breath cycle time.

FIG. 2B is a flow diagram demonstrating an example method for detecting a hypopnea in a patient, in accordance to one embodiment of the present disclosure. A hypopnea occurs when a current patient's airflow falls below 50% of the patient's previous average flow for a period of time, e.g., 10 seconds. The method discussed below may be implemented, e.g., using event detection device 140 of system 10 shown in FIG. 1.

At step 220, a patient's average airflow over a predetermined period of time or a particular number of breathing cycles may be determined, e.g., using one or more flow sensors 120. Any suitable number of breathing cycles (e.g., eight cycles) may be used. At step 222, the current patient airflow may be determined, e.g., using one or more flow sensors 120. Example methods for determining the air flow of a patient are described below with reference to FIG. 3. At step 224, the current patient airflow determined at step 222 is compared to a threshold percentage (e.g., 50%) of the average patient airflow determined at step 220. If the current patient airflow is less than the threshold percentage of the average patient airflow over a particular period of time, a hypopnea event is detected at step 226. The particular period of time can vary and can be selected as appropriate for determining the presence of a hypopnea in a particular patient. The particular period of time may be about ten seconds, for instance. However, any suitable period of time determined appropriate for indicating a hypopnea may be used. Thus, in one example, a hypopnea event may be detected if the patient's current air flow falls below 50% of the patient's average air flow for a period of ten seconds.

As discussed above, additional suitable methods for detecting respiratory events may be found in U.S. Pat. No. 6,814,074 (the "'074 patent"). By way of example, FIG. 4 of the '074 patent describes a method for detecting flow limitation events which may be used in accordance with the present invention. FIG. 6 of the '074 patent describes a method for detecting hypoventilation and hyperventilation events which may be used in accordance with the present invention. FIG. 12 of the '074 patent describes a method for detecting an acoustic vibration or snoring event which may be used in accordance with the present invention.

FIG. 3 illustrates an example method of determining a patient's airflow while the patient is using system 10 of FIG. 1 operating in bi-level mode, according to one embodiment of the present disclosure. Unlike in CPAP mode, when operating in bi-level mode, flow rate measurements of flow sensor 120 do not accurately indicate a patient's airflow because of the pressure differences used in bi-level therapy. Determining a patient's airflow is important at least because patient airflow may be used to detect the occurrence of particular respiratory events that may indicate sleep abnormalities in the patient. Identifying the existence and/or type of respiratory events experienced by a patient during sleep may aid in diagnosing and treating sleep abnormalities. The method of FIG. 3 may be implemented, e.g., in software and/or hardware associated with event detection device 140 of system 10 shown in FIG. 1A. In some embodiments, event detection device 140 may include specially designed computer logic, e.g., an ASIC, or a microprocessor based circuit including memory and embedded software, or may be a personal computer programmed to implement the method illustrated in FIG. 3.

In order to determine a patient's airflow in bi-level mode, at step 210, event detection device 140 may first detect if an exhalation has ended during a patient's breathing cycle. Techniques for detecting the end of exhalation are well known in the art and may be performed, e.g., using information provided by flow sensor 120. If it is determined that exhalation has ended, total air flow from the patient interface 110 may be measured at approximately the end of exhalation at step 312. At approximately the same time, the pressure at the patient's airway (e.g., the pressure within patient interface 110) may be measured at step 314.

At step 316, a constant k may be determined using Equation 1, which is applicable at the end of the exhalation phase when the patient's flow is expected to be zero:

$$k = \text{Total Air Flow}_1 / \sqrt{(\text{Pressure}_1)} \qquad 1.$$

Constant k represents a modification factor that can correct the total flow measured by flow sensor 120 to determine a patient's flow. The constant k may be determined using several samples of pressure and total flow measured at approximately the end of one or more expiratory phases. For instance, constant k may be calculated by based on five samples of pressure and total flow measured within 100 milliseconds before the beginning of the inspiratory phase. However, any other number of samples may be used for calculating the constant k, and each sample may be taken within any suitable time period prior to an inspiratory phase. In some embodiments, constant k may be determined over several cycles and averaged in order to obtain an average value over a period of time. Total Air Flow is the air flow measured from patient interface 110 at step 312. Pressure is the pressure measured within patient interface 110 at step 314.

Having determined the constant k, patient airflow can then be determined at step 318 using Equation 2:

$$\text{Patient Airflow} = \text{Total Air Flow}_2 - k \cdot \sqrt{(\text{Pressure}_2)} \qquad 2.$$

As discussed above regarding FIGS. 2A and 2B, Patient Airflow calculated in this manner may be used for detecting respiratory events such as apneas and hypopneas, for example.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

What is claimed is:

1. A system for determining the respiratory flow of a patient receiving respiratory therapy, the system comprising:
   a breathing device defining a breathing area;
   a flow sensor configured to take one or more measurements of the air flow through the breathing area during a time window at a transition substantially between an expiratory phase and an inspiratory phase of a breath cycle, wherein the time window is a relatively small portion of the duration of the breath cycle;
   a pressure sensor configured to take one or more measurements of the pressure in the breathing area during the time window; and
   a processor configured to:
      determine a corrective flow factor by dividing (a) a measured air flow determined based on the one or more air flow measurements taken during the time window by (b) the square root of a measured pressure determined based on the one or more pressure measurements taken during the time window, such that the determined corrective flow factor corresponds specifically to air flow and pressured measured during the time window at the transition substantially between the expiratory phase and inspiratory phase of the breath cycle;
      obtain a subsequent airflow and a subsequent pressure;
      determine a product of the corrective flow factor and a square root of the subsequent pressure; and
      determine the patient's respiratory flow by subtracting from the subsequent air flow the product of the corrective flow factor and the square root of the subsequent pressure.

2. A system according to claim 1, wherein the flow sensor is configured to take one or more measurements of the air flow during the time window by taking about five air flow measurements during a time window of about 100 milliseconds preceding the beginning of the inspiratory phase of the breath cycle.

3. A system according to claim 2, wherein the flow sensor is configured to take one or more measurements of the pressure during the time window by taking about five pressure measurements during a time window of about 100 milliseconds preceding the beginning of the inspiratory phase of the breath cycle.

* * * * *